(12) United States Patent
Hartlaub

(10) Patent No.: US 7,415,384 B2
(45) Date of Patent: *Aug. 19, 2008

(54) THERAPY MANAGEMENT TECHNIQUES FOR AN IMPLANTABLE MEDICAL DEVICE

(76) Inventor: Jerome T. Hartlaub, 2133 Erin Ct., St. Paul, MN (US) 55112

( * ) Notice: Subject to any disclaimer, the term of this patent is extended or adjusted under 35 U.S.C. 154(b) by 135 days.

This patent is subject to a terminal disclaimer.

(21) Appl. No.: 11/372,364

(22) Filed: Mar. 9, 2006

(65) Prior Publication Data

US 2006/0265140 A1    Nov. 23, 2006

Related U.S. Application Data

(63) Continuation of application No. 10/911,068, filed on Aug. 4, 2004, now Pat. No. 7,072,802, which is a continuation of application No. 10/000,712, filed on Oct. 31, 2001, now Pat. No. 6,799,149.

(60) Provisional application No. 60/259,116, filed on Dec. 29, 2000.

(51) Int. Cl.
*G06F 19/00* (2006.01)
(52) U.S. Cl. ....................................... 702/182
(58) Field of Classification Search ................ 702/182
See application file for complete search history.

(56) References Cited

U.S. PATENT DOCUMENTS

| 4,360,019 A | 11/1982 | Portner |
| 4,731,051 A | 3/1988 | Fischell |
| 4,766,542 A | 8/1988 | Pilarczyk |
| 4,784,645 A | 11/1988 | Fischell |
| 4,810,243 A | 3/1989 | Howson |
| 4,871,351 A | 10/1989 | Feingold |
| 4,985,015 A | 1/1991 | Obermann et al. |
| 5,188,106 A | 2/1993 | Nappholz et al. |
| 5,190,522 A | 3/1993 | Wojcicki et al. |
| 5,389,078 A | 2/1995 | Zalesky et al. |
| 5,417,717 A | 5/1995 | Salo et al. |
| 5,904,708 A | 5/1999 | Goedeke |
| 5,950,630 A | 9/1999 | Portwood et al. |
| 5,970,466 A | 10/1999 | Detjen et al. |

(Continued)

FOREIGN PATENT DOCUMENTS

DE      198 40 965      3/2000

(Continued)

OTHER PUBLICATIONS

PCT International Search Report, International Application No. PCT/US01/50397, mailed Dec. 9, 2002, 9 pages.

(Continued)

*Primary Examiner*—Tung S Lau
(74) *Attorney, Agent, or Firm*—Banner & Witcoff, Ltd.

(57) ABSTRACT

Disclosed is a method and apparatus for automatically adjusting drug infusion rate to optimize treatment therapy. The implantable medical device can communicate with a database or algorithm controlled by a caregiver or physician. Thus, the caregiver may request a therapy change (e.g., infusion rate versus time, pump clock settings, etc.) or a therapy management module may automatically activate the therapy change at some future time for convenience, or for technical or clinical reasons.

20 Claims, 10 Drawing Sheets

U.S. PATENT DOCUMENTS

| | | | |
|---|---|---|---|
| 6,003,006 A | 12/1999 | Colella et al. | |
| 6,088,429 A | 7/2000 | Garcia | |
| 6,201,993 B1 | 3/2001 | Kruse et al. | |
| 6,234,973 B1 | 5/2001 | Meador et al. | |
| 6,558,320 B1 | 5/2003 | Causey, III et al. | |
| 6,780,156 B2 | 8/2004 | Haueter et al. | |
| 7,072,802 B2 * | 7/2006 | Hartlaub | 702/188 |

FOREIGN PATENT DOCUMENTS

| | | |
|---|---|---|
| DE | 19840965 | 3/2006 |
| EP | 1057448 | 12/2000 |
| WO | 8401719 | 5/1984 |
| WO | WO 84/01719 | 5/1984 |
| WO | 9424929 | 11/1994 |
| WO | WO 94/24929 | 11/1994 |
| WO | 9613790 | 5/1996 |
| WO | WO 96/13790 | 5/1996 |
| WO | 9910029 | 3/1999 |
| WO | WO 99/10029 | 3/1999 |
| WO | 9944167 | 9/1999 |
| WO | WO 99/44167 | 9/1999 |
| WO | 0018449 | 4/2000 |
| WO | 0030529 | 6/2000 |
| WO | 0047108 | 8/2000 |
| WO | WO 00/47108 | 8/2000 |
| WO | 0072181 | 11/2000 |
| WO | WO 00/72181 A2 | 11/2000 |
| WO | WO 00/72181 A3 | 11/2000 |
| WO | 0148676 | 7/2001 |
| WO | 0152935 | 7/2001 |
| WO | WO 01/48676 | 7/2001 |
| WO | WO 01/52935 | 7/2001 |

OTHER PUBLICATIONS

International Search Report, International Application No. PCT/US99/26390, mailed Sep. 3, 2000, 3 pages.
PCT International Search Report, International Application No. PCT/US01/50487, mailed Aug. 26, 2002, 8 pages.
Search Report dated Aug. 1, 2006, European Patent Application No. 01988408.9, 8 pages.
PCT International Search Report mailed Aug. 26, 2002 (8 pages).
PCT International Search Report mailed Dec. 2, 2002 (9pages).

* cited by examiner

THERAPY MANAGEMENT TECHNIQUES FOR AN IMPLANTABLE MEDICAL DEVICE

This application is a continuation of U.S. patent application Ser. No. 10/911,068, filed Aug. 4, 2004, now U.S. Pat. No. 7,072,802, which is a continuation of U.S. patent application Ser. No. 10/000,712, filed Oct. 31, 2001, now U.S. Pat. No. 6,799,149, which claims priority to U.S. Provisional Application Ser. No. 60/259,116, filed Dec. 29, 2000, all of which are incorporated herein by reference in their entirety.

This patent application is related to the following co-pending patent applications, each of which having the same named inventor and filing date as the present application:

a. U.S. patent application Ser. No. 10/001,357, filed Oct. 31, 2001, now U.S. Pat. No. TBD which claimed priority to U.S. Provisional Application Ser. No. 60/259,008, filed Dec. 29, 2000;

b. U.S. patent application Ser. No. 10/000,701, filed Oct. 31, 2001, which claimed priority to U.S. Provisional Application Ser. No. 60/259,115, filed Dec. 29, 2000; and c. U.S. patent application Ser. No. 10/002,669, filed Oct. 31, 2001, which claimed priority to U.S. Provisional Application Ser. No. 60/259,022, filed Dec. 29, 2000.

Each of these related co-pending patent applications are incorporated herein by reference in their entireties.

FIELD OF THE INVENTION

This invention relates to implantable therapy delivery devices such as implantable drug delivery devices, and more particularly relates to automated therapy management systems and methods for implantable therapy delivery devices.

BACKGROUND OF THE INVENTION

The medical device industry produces a wide variety of electronic and mechanical devices suitable for use outside and inside the body for treating patient disease conditions. Devices used outside the body are termed external while devices used inside the body are termed implantable and include therapeutic substance infusion devices such as implantable drug pumps. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. Implantable therapeutic substance infusion devices can be used to treat conditions such as pain, spasticity, cancer, and a wide variety of other medical conditions.

Implantable medical devices have important advantages over other forms of therapeutic substance administration. For example, oral administration is often not workable because the systemic dose of the substance needed to achieve the therapeutic dose at the target sight may be too large for the patient to tolerate without very adverse side effects. Also, some substances simply will not be absorbed in the gut adequately for a therapeutic dose to reach the target sight. Moreover, substances that are not lipid soluble may not cross the blood-brain barrier adequately if needed in the brain. In addition, infusion of substances from outside the body requires a transcutaneous catheter, which results in other risks such as infection or catheter dislodgement. Further, implantable medical devices avoid the problem of patient noncompliance, namely the patient failing to take the prescribed drug or therapy as instructed.

Implantable medical devices are often used in conjunction with various computer and telecommunication systems and components. Information obtained by the implantable medical device may be stored and subsequently transmitted to a physician or patient caregiver or a database on demand or automatically. Many ways of using the information are known including decision making to provide optimum medical care to the person with the medical condition.

An implantable therapeutic substance infusion device such as an implantable drug delivery device is implanted by a clinician into a patient at a location appropriate for the therapy that interferes as little as practicable with normal patient activity. This location is typically a subcutaneous region in the lower abdomen. The proximal or near end of the infusion catheter is connected to the drug pump infusion outlet. The catheter is simply a flexible tube with a lumen typically running the length of the catheter. The distal or far end of the catheter is positioned to infuse a drug or drug combination to a target site in the patient. Target sights in the body included but are not limited to an internal cavity, any blood vessel, any organ, or other tissue in the body. The drug or other therapeutic substance flows from the pump via the lumen in the catheter at a programmed infusion rate to treat the disease condition. The pump typically includes an expansible reservoir for containing a refillable supply of drug. For example, U.S. Pat. No. 4,692,147 (Duggan) and U.S. Pat. No. 5,445,616 (Kratoska et al) disclose types of implantable pumps that can be used.

Examples of diseases that are treatable include spasticity and chronic intractable pain. To treat spasticity, the distal tip of the catheter is typically surgically positioned in the intrathecal space of the patient's spinal column. Drug flows out of the distal tip into the cerebral spinal fluid where it baths the spinal cord. By virtue of molecular action on nervous tissue in the spinal cord, the patient's spasticity symptoms are dramatically reduced and the patient becomes much more comfortable and competent. Pain patients are treated in much the same way.

The infusion rate of the drug pump is typically programmed to be variable over time. The rate is usually controlled by certain components in the pump. The controlled infusion rate is often further set by using an external device or programmer to transmit into the pump, instructions for the controlled infusion. The controlled infusion may be variable as time passes according to the needs of the patient. The instructions provided to the pump to control the infusion rate of the drug pump are typically determined by a medical person. In some cases the patient is able to provide the instructions to the pump via an external patient-programming device. In contrast, fixed rate pumps usually cannot be programmed and are only capable of constant infusion rate.

Once implanted, the implantable medical device will require re-programming to account for changes in the desired therapy, changes in the condition being treated, or changes in the placement of the lead delivering the therapy to the body. This can be accomplished in any number of ways including, for example, the patient may manually adjust the treatment therapy, or the treating physician may manually adjust or re-program the implanted device. In either of these cases, there is no mechanism by which the implanted device may automatically make therapy adjustments or store prior therapy changes for later use and analysis.

It is therefore desirable to provide an implantable therapy delivery system that is capable of automatically making therapy adjustments. It is also desirable to provide an implantable therapy delivery system that provides historical information relating to the therapy changes made to the implanted devices.

BRIEF SUMMARY OF THE INVENTION

In accordance with a preferred embodiment of the present invention, the drug infusion rate is automatically adjusted by communicating with an outside-the-pump database or algorithm, the latter controlled by a caregiver or physician or through use of an expert system database. Thus, the caregiver may request a therapy change (e.g., infusion rate versus time, pump clock settings, etc.) for a patient in real time while a Drug Pump Management Controller System (DPMCS) or a therapy management module may automatically activate the therapy change at some future time for convenience, or for technical or clinical reasons. Technical reasons may include, for example, where routine accessibility to the patient is difficult. The therapy management module may have direct control to reprogram the pump and/or may provide recommendations to the caregiver/physician.

Alternatively, the pump may automatically detect (or with the addition of patient message to the pump) that the therapy is not giving acceptable results, and the pump/system would automatically inform the caregiver/physician of this status.

The pump preferably is coupled to one or more sensors to sense physiologic or other characteristics of the patient to automatically provide closed-loop feedback control. The automated data acquisition (e.g., therapy parameters, physiologic parameters, etc.) would be possible by storing any changes to the therapy in a database.

The objects, advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

In accordance with the present invention, an implantable therapy delivery device is equipped with automated management control capabilities. Although not required, the invention will be described in part in the general context of computer-executable instructions, such as program modules. Generally, program modules include routines, programs, objects, scripts, components, data structures, etc. that perform particular tasks or implement particular abstract data types. Program modules may be part of a single software program or may be implemented as separate software programs.

Figure 1:
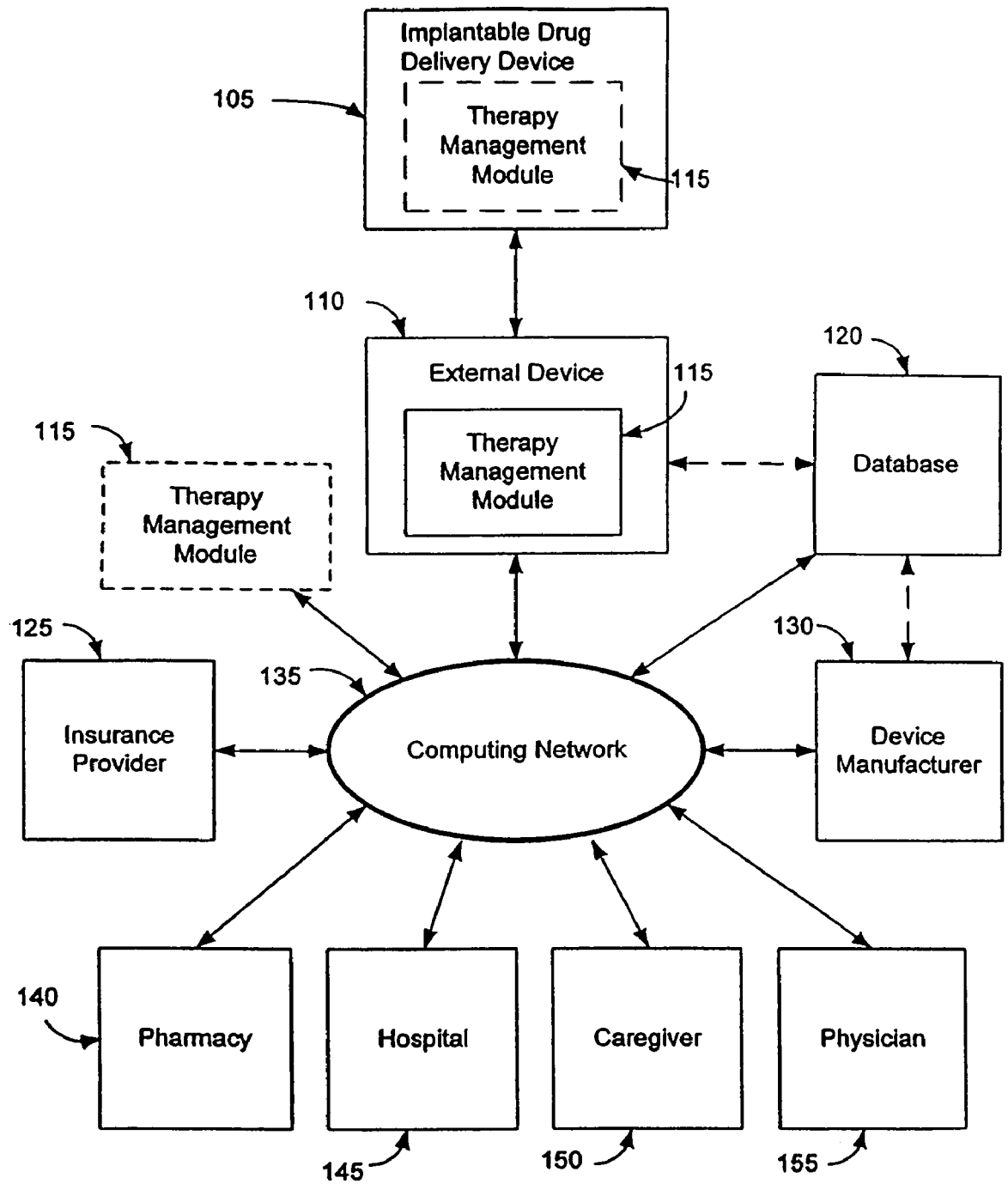
FIG. 1 is a schematic block diagram of an overall system for therapy management of an implantable therapy delivery device in accordance with a preferred embodiment of the present invention.

FIG. 1 is a schematic block diagram of an overall system for therapy management of an implantable therapy delivery device in accordance with a preferred embodiment of the present invention. The overall system generally includes an implantable therapy delivery device 105 implantable within a patient, an external device or programmer 110 having a therapy management module 115 in accordance with a preferred embodiment of the present invention, a database 120, and a computing network 135 such as the Internet coupled to various entities involved in the healthcare management of the patient. Such entities may include, for example, an insurance provider 125, a pharmacy 140, a hospital 145, a caregiver 150, a physician 155, and/or a device manufacture 130. In alternative embodiments, the therapy management module 115 may be implemented in other parts of the overall system for therapy management including, for example, in the implantable therapy delivery device 105, or on a server accessible over the computing network 135. Further details of the therapy management module are discussed in further detail herein. The implantable therapy delivery device 105 may be an implantable drug pump or an implantable pulse generator or both. The implantable therapy delivery device 105 is coupled to be in bi-directional communication with the external device 110 via telemetry. The external device 110 may be any computing device capable of communicating with the implantable therapy delivery device 105, including for example, a physician programmer, a patient programmer, a screening device, a data acquisition device, and the like. The bidirectional communications may be of any type of telemetry including RF.

The external device 110 is preferably coupled to the computing network 135 for communicating with various healthcare entities essential to the management of the treatment therapy of the patient. Also coupled to the network 135 and in communication with the external device 110 is the database 120 storing therapy management information relating to the patient. The computing network 135 may be, for example, a public network such as the Internet, an intranet, an extranet, or a private network. The computing network 135 enables the external device 110 to communicate with the various healthcare entities and the database 120.

The external device 110 may be coupled to the computing network 135 either directly through a modem or may be networked to a personal computer that is coupled to the computing network 135 through known techniques. The various other entities 125, 130, 140-155 are preferably coupled to the computing network 135 via a general-purpose computing device. The computing devices used by these entities preferably have installed therein a software application that communicates with the drug management module to perform the various scheduling functions to be performed.

Figure 2:
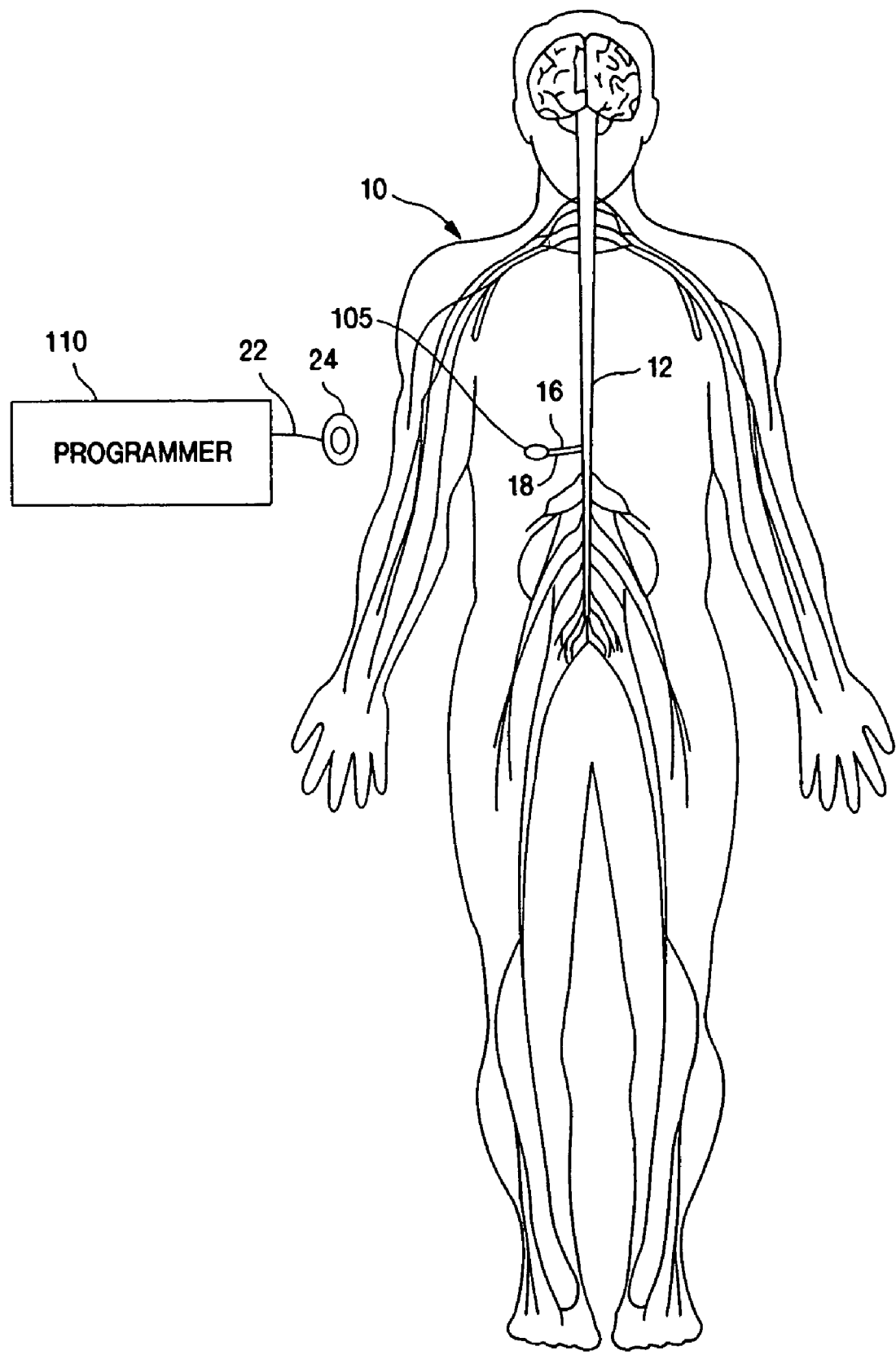
FIG. 2 is a diagrammatic view of a drug delivery device for use with the present invention as implanted within a patient.

As discussed, implantable drug delivery devices are generally known in the art. U.S. Pat. No. 4,692,147 (Duggan) and U.S. Pat. No. 5,445,616 (Kratoska et al), for example, illustrate the general features of these devices. FIG. 2 is a diagrammatic illustration of an exemplary implantable drug delivery device 105 for use with the present invention. The system includes the device 105 that may be implanted below the skin of a patient 10 in the abdomen or any other location of the body. The device 105 is typically a pump that delivers drug to a catheter 16/18 that is positioned to deliver the drug to specific infusion sites within the patient's body (in this case, the spinal cord 12). The distal end of the catheter 16/18 terminates in a cylindrical hollow tube having a distal end implanted into a portion of the body by conventional surgical techniques. The catheter 16/18 is joined to the implanted device 105 in the manner shown, and may be secured to the device 105 by, for example, screwing the catheter 16/18 onto a catheter port of the device 105.

The implantable system 105 may include one or more sensors to provide closed-loop feedback control of the drug delivery system to provide enhanced results. Sensors can be used with a closed loop feedback system to automatically determine the level of treatment therapy necessary to alleviate the symptoms of the disorder being treated. The sensor is attached to or implanted into a portion of a patient's body suitable for detecting symptoms of the disorder being treated, such as a motor response or motor behavior. The sensor is adapted to sense an attribute of the symptom to be controlled or an important related symptom. For movement disorders that result in abnormal movement of an arm of the patient, such as an arm, the sensor may be a motion detector implanted in the arm. For example, the sensor may sense three-dimensional or two-dimensional motion (linear rotational or joint motion), such as by an accelerometer. One such sensor suitable for use with the present invention is described in U.S. Pat. No. 5,293,879 (Vonk). The sensor also may be placed in the implantable drug delivery device, for example, to sense drug levels. Those skilled in the art will appreciate that any type of sensor may be utilized with the present invention. The output of the sensor may be coupled by a cable or via telemetry to the input of an analog to digital converter within the implantable drug delivery device. Alternatively, the output of an external sensor would communicate with the implantable drug delivery device through a telemetry downlink.

Figure 3:
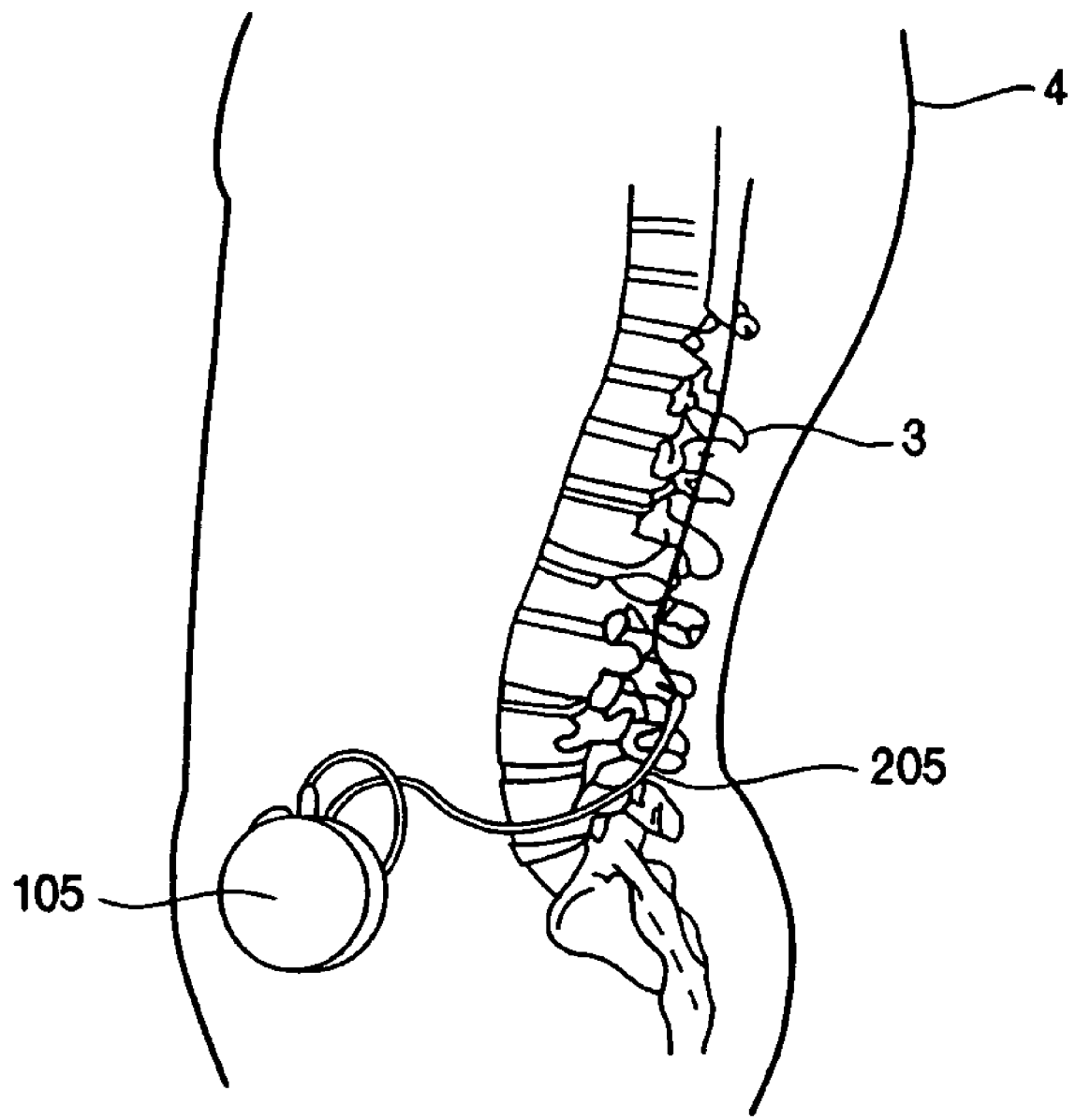
FIG. 3 illustrates a typical position in a patient of an implantable drug delivery device with a catheter implanted at or near a spinal cord.
Figure 4:
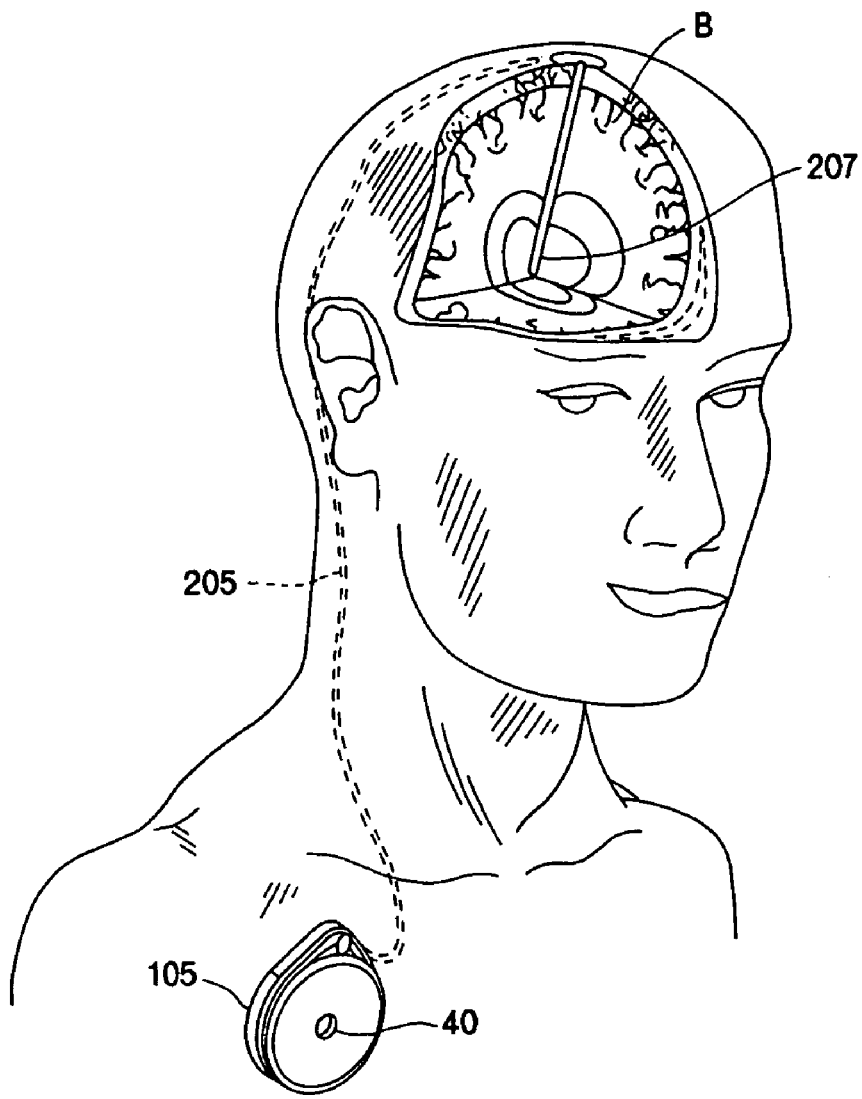
FIG. 4 illustrates another typical position in a patient of an implantable drug delivery device with a catheter implanted at or near a brain.
Figure 5:
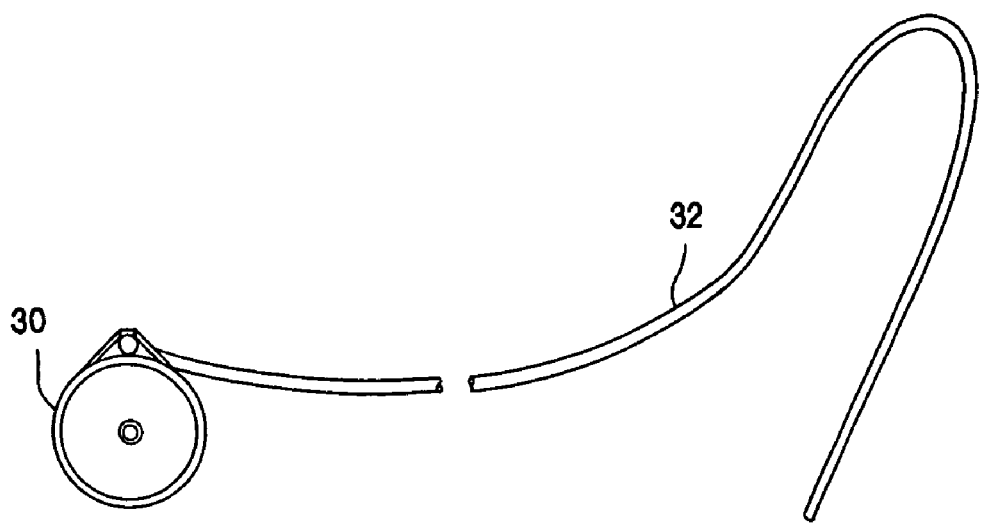
FIG. 5 depicts the implantable drug delivery device.

The implantable drug delivery device 105 can be used for a wide variety of therapies to treat medical conditions (also known as medical indications) such as pain, spasticity, cancer, and many other medical conditions. The implantable drug delivery device 105 is typically implanted by a clinician, such as a surgeon, using a sterile surgical procedure performed under local, regional, or general anesthesia. Before implanting the therapeutic substance infusion device, a catheter is typically implanted with the distal end position at the desired therapeutic substance infusion site and the proximal end tunneled to the location where the therapeutic substance infusion device is to be implanted. The implantable therapeutic substance infusion device is generally implanted subcutaneously about 2.5 cm (1.0 inch) beneath the skin where there is sufficient subcutaneous tissue to support the implanted system. As one example, FIG. 3 illustrates the implantable drug delivery device 105 coupled to catheter 205, both of which are under the surface of the skin 4. The catheter 205 is positioned with its distal tip in the intrathecal space of the spinal column 3. As another example, FIG. 4 shows the implantable drug delivery device 105 for infusion of drug into to brain B. The device 105 is coupled to catheter 205 with a distal end terminating within the brain B. FIG. 5 illustrates the various components of the implantable drug delivery device 105 that are implanted within the patient 10.

Once the therapeutic substance infusion device is subcutaneously implanted into the patient, the incision can be sutured closed and the therapeutic substance infusion device can begin operation. The implantable drug delivery device 105 operates to infuse a therapeutic substance at a programmed rate into a patient. The therapeutic substance is a product or substance intended to have a therapeutic effect such as pharmaceutical compositions, genetic materials, biologics, and other substances. Pharmaceutical compositions are chemical formulations intended to have a therapeutic effect such as intrathecal antispasmodics (e.g., balcofen), pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like. As used herein, the term drug shall refer generally to any therapeutic substance.

The therapeutic substance can be replenished in some embodiments of the implanted therapeutic substance infusion device by inserting a non-coring needle connected to a syringe filled with therapeutic substance through the patient's skin into a septum and into a reservoir in the therapeutic substance infusion device to fill the implanted device reservoir. Refill kits are available which include the drug and all other necessary equipment needed for the medical attendant to refill the pump.

A therapeutic substance bolus can be administered by a clinician, in some embodiments, by inserting a non-coring needle connected to a syringe into a catheter access port. This procedure can be used for several other reasons including reopening the catheter if it becomes occluded or to withdraw a sample of cerebral spinal fluid for investigative purposes.

Figure 6:
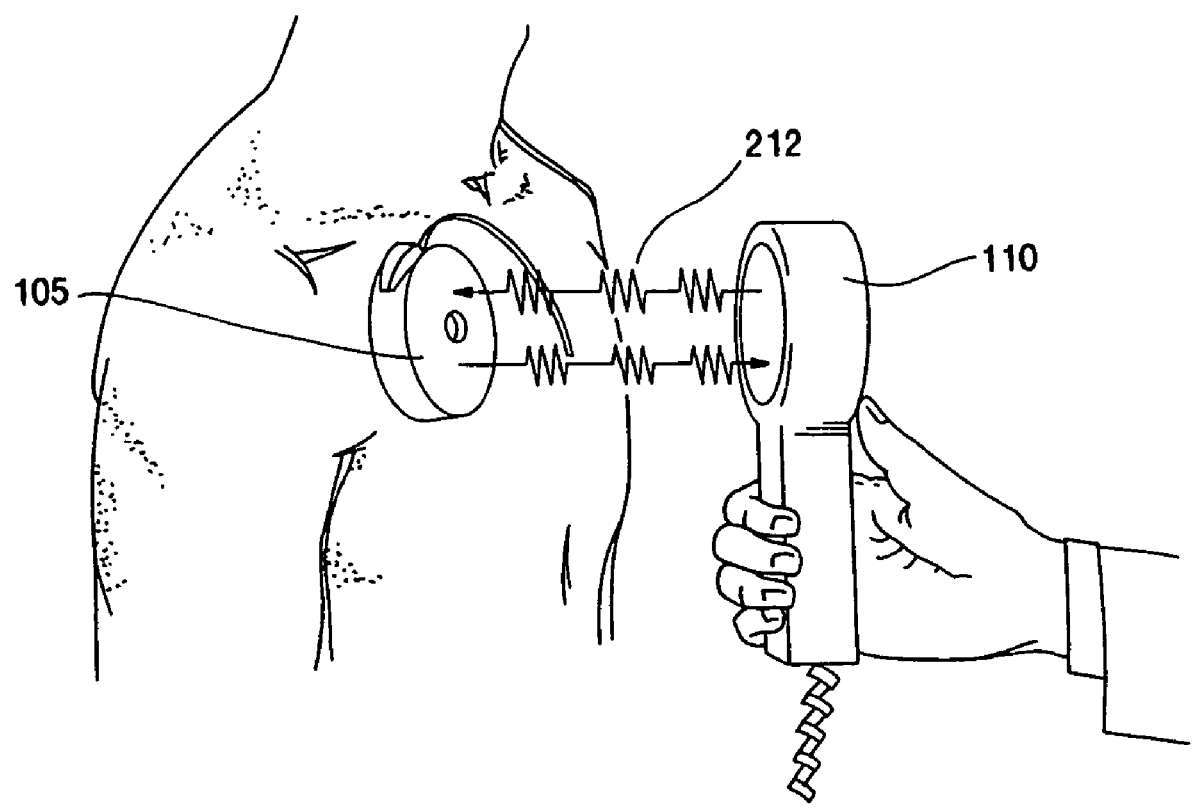
FIG. 6 shows an implantable pump communicating via telemetry with an external handheld programming device.

FIG. 6 illustrates a typical pump programming technique. An external device, a handheld programming device 110 in this embodiment, transmits and receives radio frequency signals 212 to and from the implantable drug delivery device 105. The radio frequency signals 212 sent to the pump, often called the downlink signal, contain the programming instructions needed by the implantable drug delivery device 105 for it to correctly infuse a drug into the patient from its drug reservoir. Many other types of information may be sent to the pump including requests for information residing in the pump in accordance with the present invention (discussed herein).

The implantable drug delivery device 105 may continuously or periodically store various types of information including, for example without limitation, pump diagnostics, drug delivery information, batter life, etc. Further, the implantable drug delivery device 105 may receive information from various sensors inside the pump or information from sensors integral with the catheter, thereby obtaining physiological information about the patient. Even further, the implantable drug delivery device 105 may store historical data about the drug infusing profile, patient requests for more drug or other such information.

Such information stored in the pump may be valuable to the treating physician and/or the medical device supplier and can be retrieved from the pump. In particular, the information stored in the implantable drug delivery device 105 may be retrieved in response to a request by the pump from the programming device 110. After the request is received and processed in the implantable drug delivery device 105, the implantable drug delivery device 105 prepares the requested information and sends it to the programming device 110, sometimes called uplink data. The pump information received by the programming device 110 is processed and converted to intelligible data for clinical or technical use. This intelligible data can be used for many purposes including management of the pump performance, management of the patient therapy, and/or other medical or record-keeping purposes.

Figure 7:
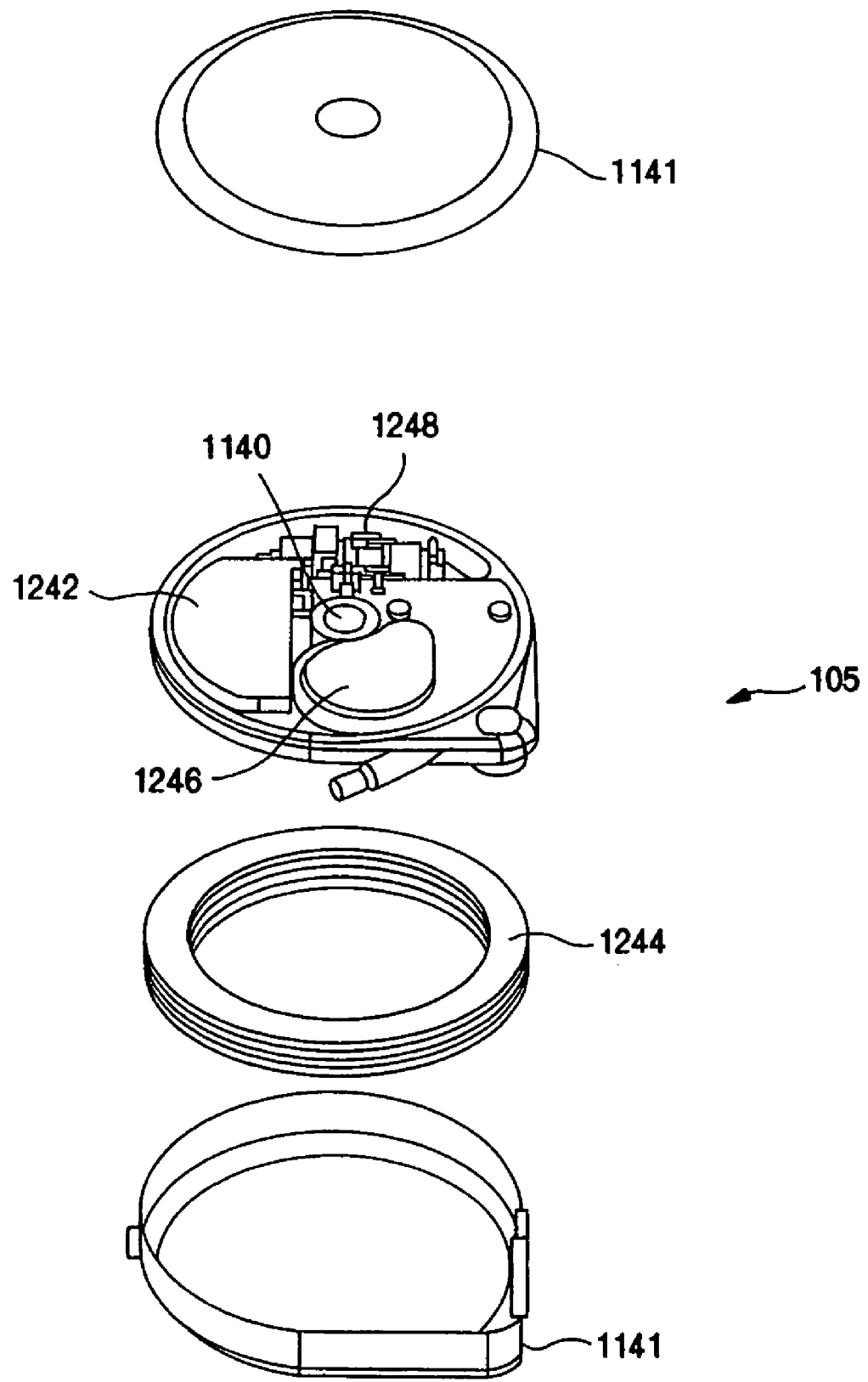
FIG. 7 is a diagrammatic view of an exemplary implantable drug delivery device for use with the present invention depicting the various layered components of the device.
Figure 8:
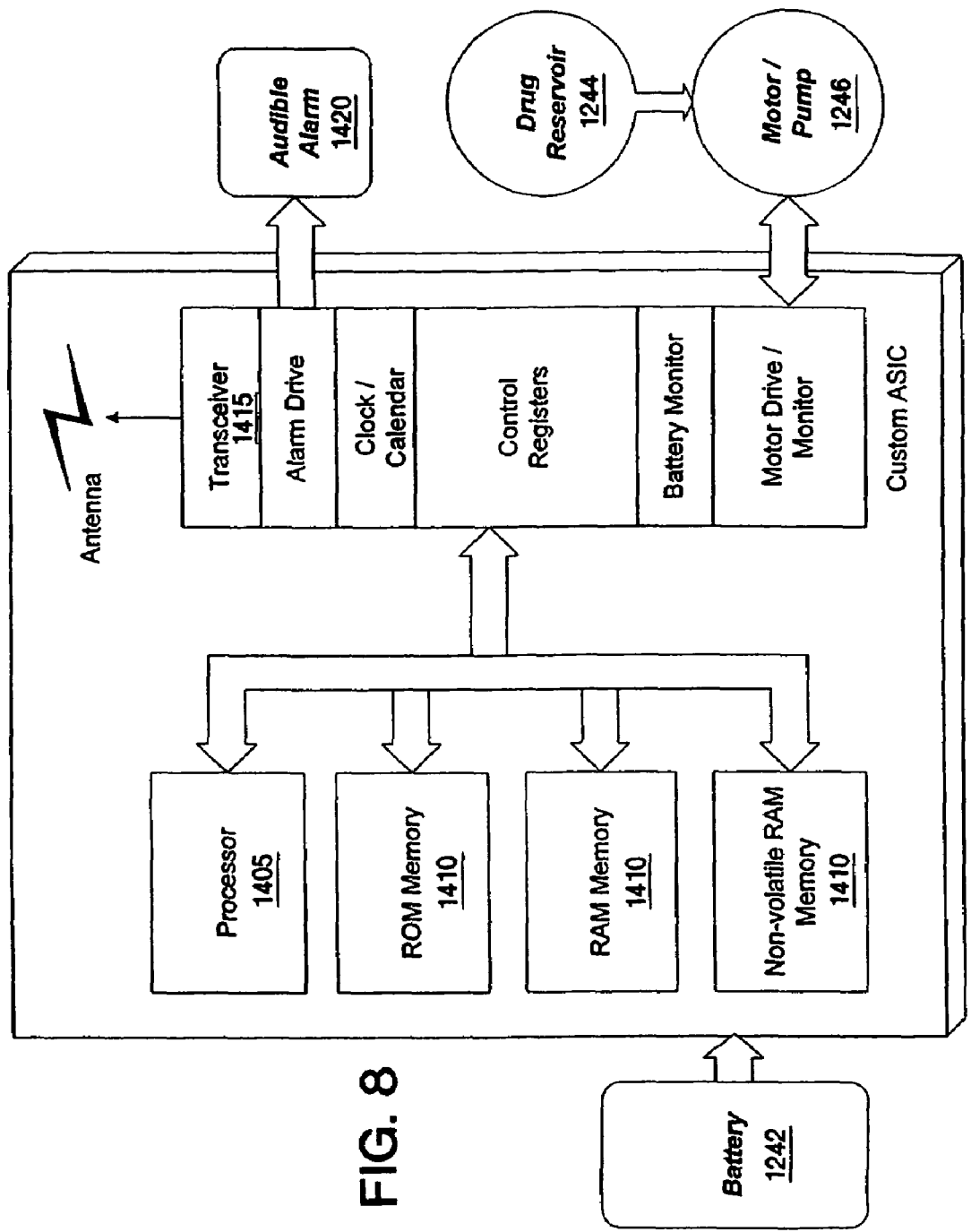
FIG. 8 shows a block diagram of an implantable drug delivery device embodiment for use with the present invention.

Referring back to the embodiment of the implantable drug delivery device, the present invention may be implemented for use any number of such devices. FIG. 7 show one such example of the implantable drug delivery device 105 and FIG. 8 shows a block diagram of the implantable drug delivery device 105. The implantable drug delivery device 105 generally comprises a housing 1141, a power source 1242, a therapeutic substance reservoir 1244, a therapeutic substance pump 1246, and electronics 1248. The housing 1141 is manufactured from a material that is biocompatible and hermetically sealed such as titanium, tantalum, stainless steel, plastic, ceramic, and the like. The power source 1242 is carried in the housing 1141. The power source 1242 is selected to operate the therapeutic substance pump 1246 and electronics 1248 such as a lithium ion (Li+) battery, capacitor, and the like.

The therapeutic substance reservoir 1244 is carried in the housing 1141. The therapeutic substance reservoir 1244 is configured for containing a therapeutic substance. The therapeutic substance reservoir 1244 may be refilled with therapeutic substance while implanted via port 1140. The therapeutic substance pump 1246 is carried in the housing 1141. The therapeutic substance pump 1246 is fluidly coupled to the therapeutic substance reservoir 1244 and electrically coupled to the power source 1242. The therapeutic substance pump 1246 is a pump that is sufficient for infusing therapeutic substance such as a piston pump, a peristaltic pump that can be found in the SynchroMed® Infusion System available from Medtronic, Inc., or a pump powered by a stepper motor, an AC motor, a DC motor, an electrostatic diaphragm, a piezoelectric diaphragm, a piezoelectric motor, a solenoid, a shape memory alloy, and the like.

The electronics 1248 are carried in the housing 1141 and coupled to the therapeutic substance pump 1246 and the power source 1242. The electronics 1248 include a processor 1405, memory 1410, an infusion program in memory, and transceiver circuitry 1415. The processor 1405 can be an Application Specific Integrated Circuit (ASIC) state machine, a gate array, controller, and the like. The electronics 1248 are configured to control the infusion rate of the therapeutic substance pump 1246 and can be configured to operate many other features such as patient alarms 1420 and the like. The infusion program resides in memory and is capable of being modified once the implantable drug deliver device is implanted. The transceiver circuitry 1415 is coupled to the processor 1405 for externally receiving and transmitting therapeutic substance infusion device information.

As discussed, the present invention is implemented in part the general context of computer-executable instructions, such as program modules. In a preferred embodiment as discussed herein, some of the features of the present invention are implemented within a therapy management module 115. The implantable device 105 would provide via telemetry the necessary information for the external device 110 to provide the therapy management functionality of the present invention. In the embodiment where the therapy management module 115 is within the implantable device 105, it may be found in the electronics 1248.

Figure 9:
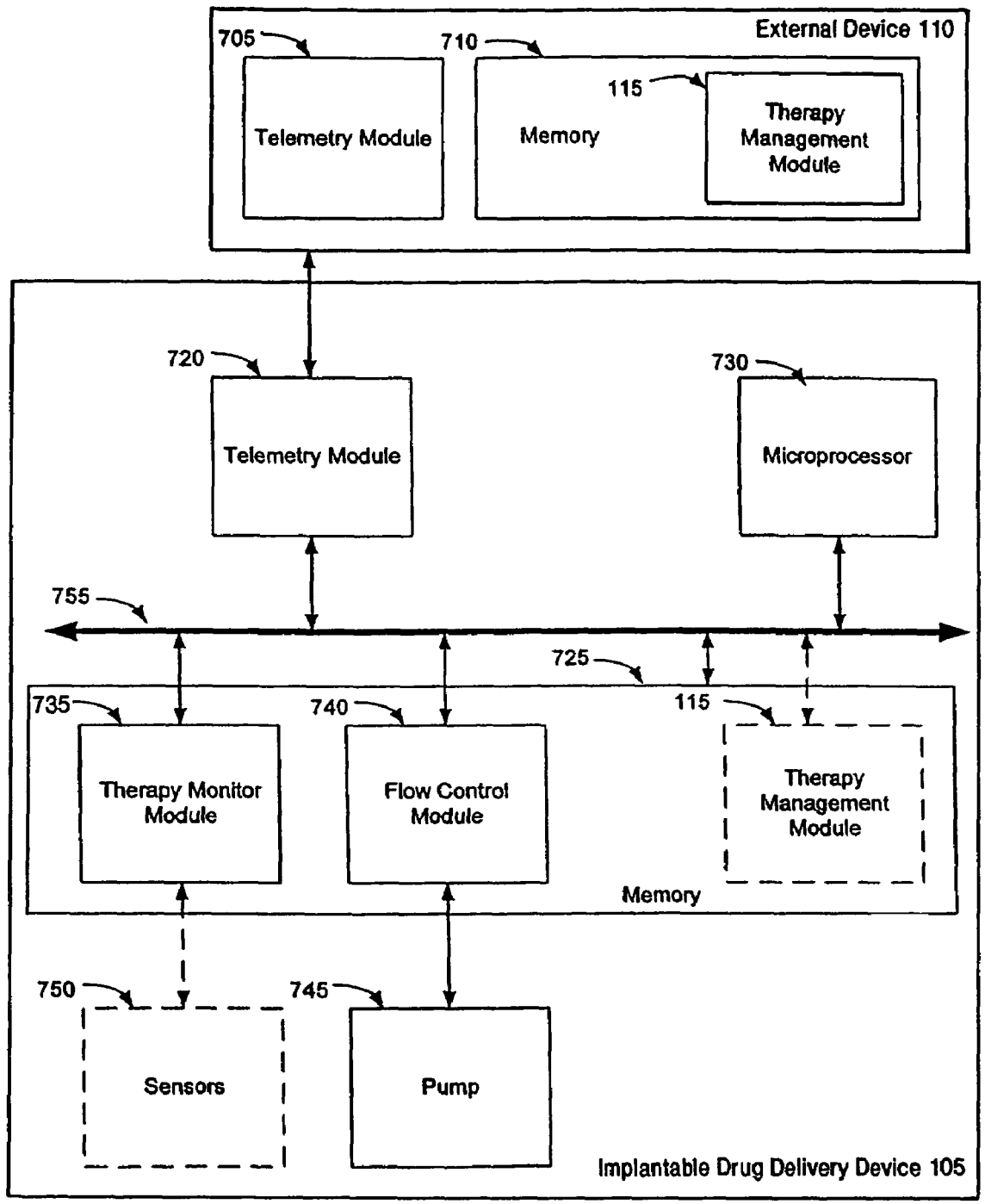
FIG. 9 is a schematic block diagram of the electronic modules of the implantable drug pump in accordance with a preferred embodiment of the present invention.

Referring to the schematic block diagram of FIG. 9, the implantable device 105 includes various electrical and software components including a microprocessor 730, a flow control module 740 for controlling the flow of drug from the reservoir to the infusion port, a telemetry module 720 for providing bidirectional communication between the implantable device 105 and the external device 110, a memory 725 for storing the various software modules for use with the present invention, a therapy monitor module 735, and (optionally) a therapy management module 115. The therapy monitor module 735 provides one or more performance parameters related to therapy management including, but not limited to, drug flow rate, drug quantity in reservoir, drug type, drug usage history, etc. Drug usage monitored by the therapy monitor module 735 may include, for example and without limitation, the quantity drug consumed by the patient, the rate in which the drug is being consumed by the patient, and the estimated date that the drug in the pump will be exhausted based on the previous two parameters. Drug usage may be determined, for example, by way of a pump reservoir sensor 750 that senses the amount of drug remaining in the pump reservoir. For example, the pump reservoir sensor 750 disclosed in U.S. Pat. No. 6,099,495, having application Ser. No. 09/070,255, filed Apr. 30, 1998, and entitled "Reservoir Volume Sensor", may be used.

The external device 110 generally includes a telemetry module 705 and a memory 710 for storing various software applications and modules for use with the present invention. Stored within the external device 110 is the therapy management module 115. The therapy management module 115 gathers data regarding the implantable device 105 to make decisions regarding the management of medical therapy. Such decisions include, but are not limited to, reprogramming of the implanted device 105, warnings associated with the therapy to the patient/caregiver/physician, changed drug formulations, etc. The patient/caregiver/physician are automatically notified of any such changes. Provisions in the system allows for confirming or other responses to insure adequate communication and commitment for action. All data and fiducial markers (e.g., date, requester) are sent to database 120 for archive and potential later retrieval.

Database 120 includes a human clinical records database of therapy performance related to various indications and various drug used to treat those indications. This database 120 is likely generated from various sources, including previous pump patient experience, and is constantly updated and managed. This database is preferably accessible by the therapy management module 115.

The pump telemetry data is obtained by or through the external device 110 that is held in reasonable proximity with the pump 105 implanted within patient. The external device 110 interrogates the implanted pump 105 and information is uplinked from the pump 105 to the external device 110. In addition, data from the pump is provided to the therapy management algorithm 830 (discussed herein).

Figure 10:
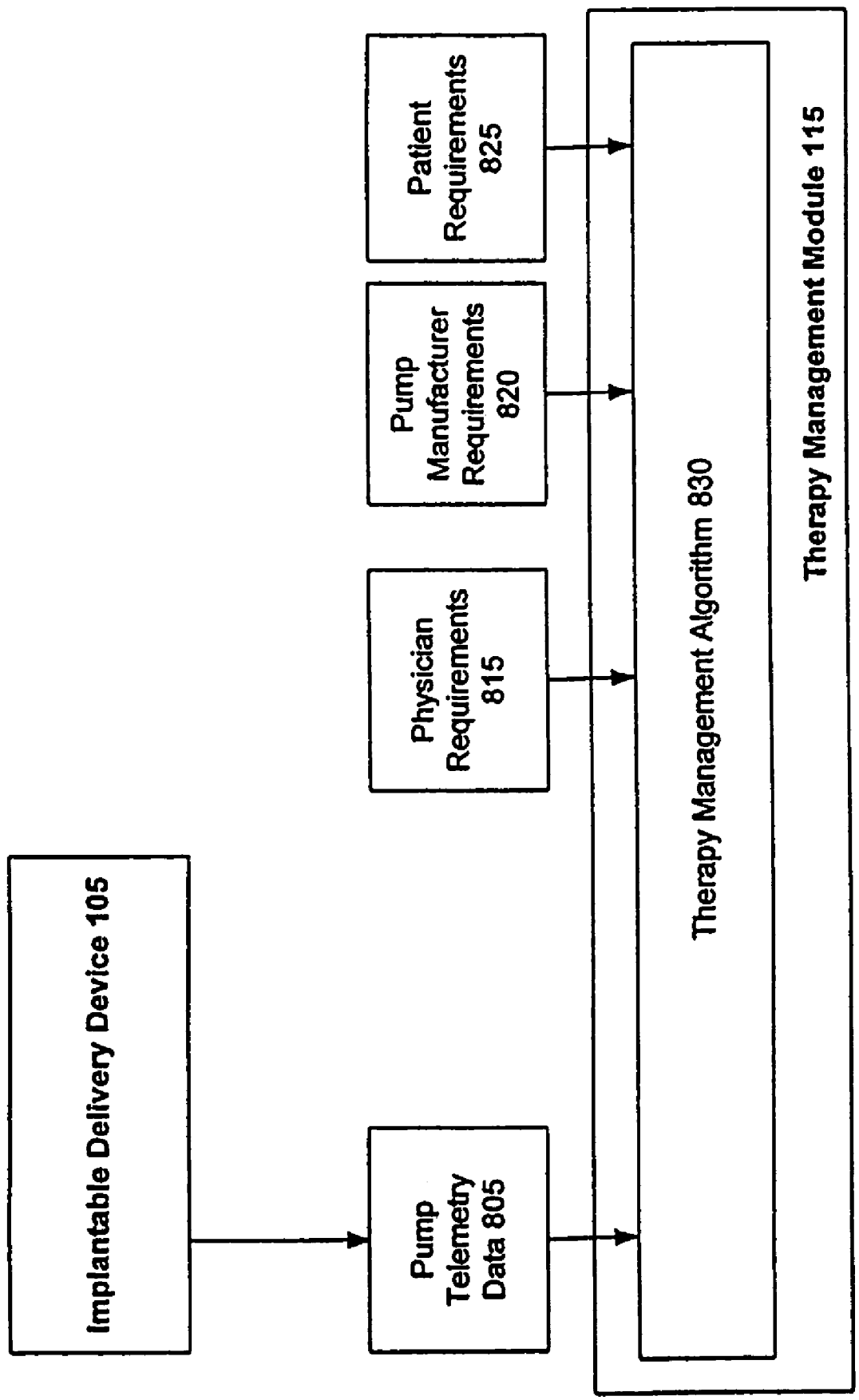
FIG. 10 is a schematic block diagram of the therapy management module of the implantable drug pump in accordance with a preferred embodiment of the present invention.

As shown in the block diagram of FIG. 10, the data regarding the implantable device 105 that the therapy management module 115 uses to make its determination include, for example, pump performance information from the therapy monitor module 735, pump manufacturer requirements 820, physician requirements 815, and patient requirements 825. The pump manufacturer requirements 820 preferably provides a continuous real time input to the therapy management module 115 to allow the pump manufacturer to specify limits for changing therapy parameters to conform with the design of the implanted device 105. The physician and patient requirements 815 and 825 include requirements of the drug therapy that are selectable and generally specific to the patient and/or physician therapy preferences (e.g., flow rate). These requirements 815 and 825 are determined by the physician who may input these requirements via a general-purpose computing device. The therapy management algorithm 830 receives the requirement information 815-825 either by manual entry of the information or could be downloaded via the Internet, a local network, or a telephone line. For archival purposes, all data is stored in database 120.

Still referring to FIG. 10, the therapy management module 115 includes a therapy management algorithm 830 that serves to determine the management of the medical therapy provided to the patient.

Figure 11:
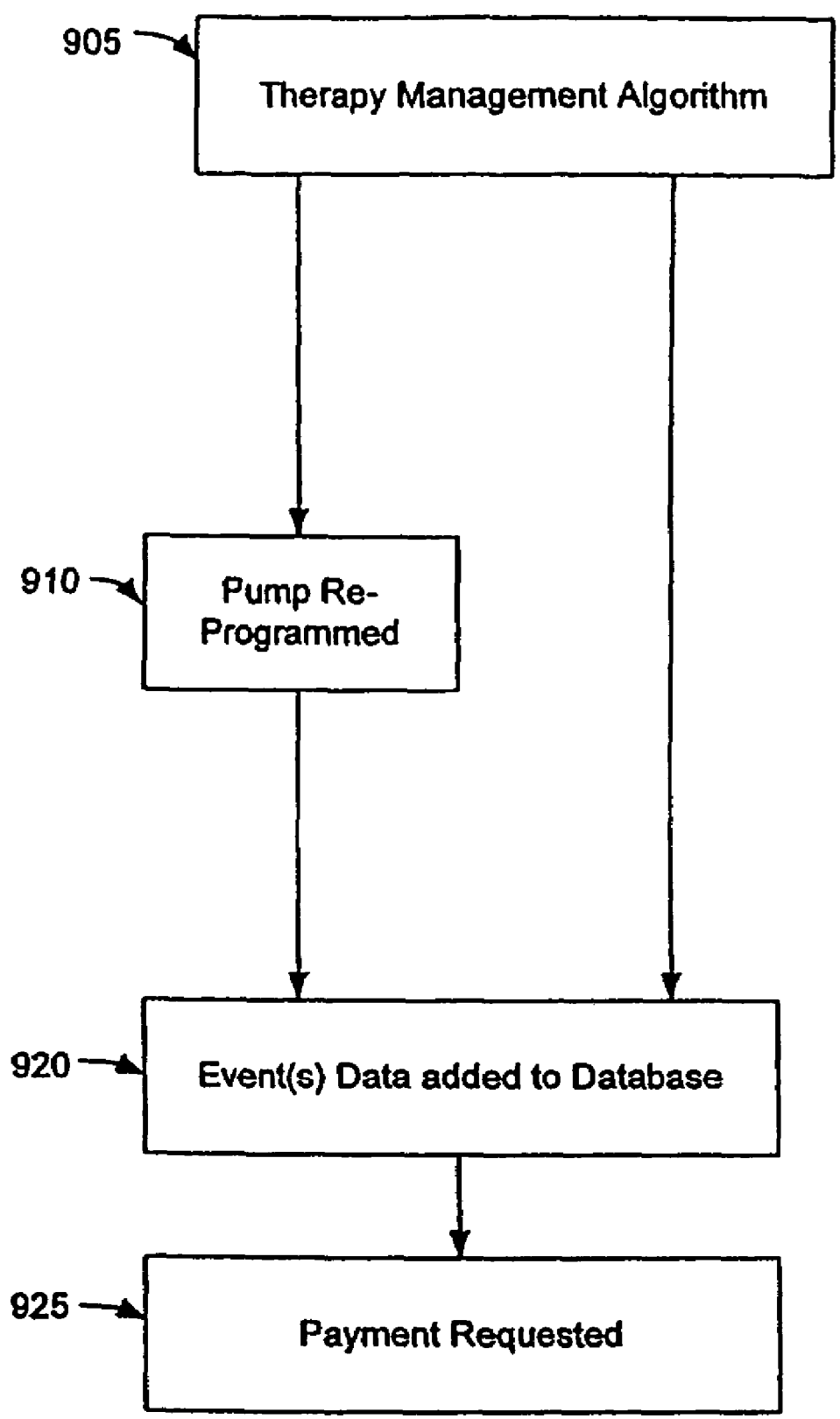
FIG. 11 is a flow chart depicting the process for determining whether therapy in the implantable device to be refilled in accordance with a preferred embodiment of the present invention.

FIG. 11 is a flow chart illustrating the procedure followed by the therapy management module 115. As discussed above, the therapy management module 115 utilizes a therapy management algorithm 830 to make this determination. At step 905, the therapy management algorithm 830 determines whether a therapy change is needed. The therapy management module 115 may make this determination either continuously, periodically (e.g., on a daily basis), or even manually (e.g., manually interrogating the implantable device 105 for it's drug status and drug infusion rate conditions). If a therapy change is not required, a record that this determination was made is stored in the database 120 (at step 920). On the other hand, if the therapy management algorithm 830 determines that a therapy change is required, at step 910, the therapy management module 825 performs a reprogramming of the pump 105. At step 920, event data (such as the therapy change) are stored in the database 120. Finally, at step 925, whether or not the therapy is changed, the therapy management algorithm 830 requests payment for the therapy management service.

For example, in one embodiment, the sensor data from sensor 750 could be body vibration or activity information when the body vibration is due to tremor in an extremity. The therapy management algorithm 830 compares this sensor output or level of tremor to the physician requirements 815 which may be a low level of tremor and if the tremor level is too great, either in frequency or amplitude or some combination, the therapy management algorithm 830 could decide that a therapy change is needed. This information is transmitted to database 120 and the pump 105 is reprogrammed to infuse a larger amount of the antitremor agent. Alternatively, if the tremor level is not so great so as to require a therapy change, then this information is communicated to the database 120 and the pump 105 is not reprogrammed to infuse additional drug. Thus, in this example, a main decision the therapy management algorithm 830 makes is to compare the physician requirements 815 for the level of tremor to what they pump 105 actually senses is the tremor level. A decision is then made by the therapy management algorithm 830 as to whether to reprogram the pump for additional drug infusion.

When the event is added to the database 120, the therapy management algorithm 830 decides whether a payment request for this therapy management procedure should be made or whether payment request should be made, depending on whether the pump 105 is reprogrammed.

In another embodiment, the physician requirements 815 could be replaced with clinical data guidelines information. The therapy management algorithm 830 and all other elements of the flow chart would be the same with the exception that the therapy management algorithm 830 would use the clinical data guidelines to determine whether or not the pump should be reprogrammed. Alternatively, the physician requirements 815 could be used in a secondary level with the clinical data guidelines as a primary reference for the therapy management algorithm 830.

When the therapy management algorithm 830 makes a decision for pump programming, it is accomplished using the external device 110 being placed in reasonable proximity to the pump 105 in the patient.

It will be appreciated that the present invention may be implemented using other embodiments. Those skilled in the art recognize that the preferred embodiments may be altered and modified without departing from the true spirit and scope of the invention as defined in the appended claims.

I claim:

1. An implantable drug delivery system having a data delivery feature, comprising:
   an external device;
   a housing;
   a drug reservoir positioned in the housing and configured to contain a therapeutic substance;
   an infusion port in fluid communication with the drug reservoir;
   a pump configured to direct the therapeutic substance from the drug reservoir to the infusion port; and
   electronics coupled to pump and configured to control the flow of therapeutic substances from the drug reservoir to the infusion port, the electronics including a memory configured to store performance information and programming, the electronics further configured to monitor the flow of the therapeutic substance, wherein the electronics is configured to be in bi-directional communication with the external device and to provide performance information from the memory to the external device and to receive changes to the programming in the memory from the external device.

2. The implantable drug delivery system of claim 1, further comprising a sensor configured to provide feedback to the electronics.

3. The implantable drug delivery system of claim 1, wherein the external device is configured to be coupled via a network to at least one entity selected from a group consisting of an insurance provider, a pharmacy, a hospital, a caregiver, a physician and a device manufacture.

4. The implantable drug delivery system of claim 1, wherein the external device comprises a data-acquisition device.

5. The implantable drug delivery system of claim 1, further comprising a catheter with a distal end extending from the housing, wherein catheter is fluidly coupled to the drug reservoir and the distal end is coupled to the infusion port.

6. The implantable drug delivery system of claim 1, wherein the pump is positioned in the housing.

7. The implantable drug delivery system of claim 1, further comprising a pump reservoir sensor.

8. The implantable drug delivery system of claim 1, wherein the external device is in communication with a database, the database including algorithms for modifying the programming of the electronics based on performance data provided to the external device.

9. The implantable drug delivery system of claim 2, wherein the electronics is configured to modify the flow of the therapeutic substance in response to the feedback and the programming in the memory.

10. The implantable drug system of claim 3, wherein the network includes a connection over an Internet.

11. The implantable drug delivery system of claim 3, wherein the network includes a connection over a land-based line.

12. An implantable drug delivery device, comprising:
 a housing;
 a drug reservoir positioned in the housing and configured to contain a therapeutic substance;
 an infusion port in fluid communication with the drug reservoir;
 a pump in the housing, the pump configured to direct the therapeutic substance from the drug reservoir to the infusion port;
 electronics coupled to the pump and configured to control the flow of therapeutic substances from the drug reservoir to the infusion port, the electronics including a memory configured to store performance information and programming, the electronics further configured to monitor the flow of the therapeutic substance and to communicate with an external programmer via a network so that performance information of the implanted drug delivery device can be reported and programming on the device can be modified based on the performance information; and
 a sensor configured to in provide feedback to the electronics; wherein the electronics is configured to accept programming via telemetry so as to control whether the therapeutic substance is delivered through the infusion port based on the feedback received from the sensor.

13. The implantable drug delivery system of claim 12, wherein the network is an Internet.

14. The implantable drug delivery system of claim 12, wherein the network includes a connection over a land-based line.

15. The implantable drug delivery system of claim 12, wherein external programmer comprises a database.

16. The implantable drug delivery system of claim 15, further comprising a pump reservoir sensor.

17. An implantable drug delivery device, comprising:
 a housing;
 a drug reservoir positioned in the housing and configured to contain a therapeutic substance;
 an infusion port in fluid communication with the drug reservoir;
 a pump configured to direct the therapeutic substance from the drug reservoir to the infusion port;
 a microprocessor positioned in the housing and configured to control the pump, the microprocessor including a memory configured to store performance information and programming, the microprocessor further configured to monitor the flow of the therapeutic substance and to use bi-directional communication with an external programmer so that performance information of the implanted drug delivery device can be reported and programming on the device can be modified based on the performance information.

18. The implantable drug delivery system of claim 17, wherein the microprocessor is configured to communication with the external programmer via an Internet connection.

19. The implantable drug delivery system of claim 17, further comprising a sensor configured to sense characteristics of a patient, wherein the microprocessor is configured to receive signals received from the sensor and store them in the memory.

20. The implantable drug delivery system of claim 19, wherein the microprocessor is configured to determine whether a therapy change is needed based on the signals received from the sensor.

* * * * *